(12) United States Patent
Karmaker et al.

(10) Patent No.: US 7,168,952 B2
(45) Date of Patent: Jan. 30, 2007

(54) ENDODONTIC POST AND OBTURATING SYSTEM

(75) Inventors: Ajit Karmaker, Wallingford, CT (US); Larry A. Lopez, 522 Plesant Vally Dr. N., Boerne, TX (US) 78006; Bruce Alpert, Madison, CT (US); Bruce A. Finnigan, Wallingford, CT (US)

(73) Assignees: Pentron Clinical Technologies, LLC, Wallingford, CT (US); Larry A. Lopez, San Antonio, TX (US)

( * ) Notice: Subject to any disclaimer, the term of this patent is extended or adjusted under 35 U.S.C. 154(b) by 0 days.

(21) Appl. No.: 10/633,612

(22) Filed: Aug. 1, 2003

(65) Prior Publication Data

US 2005/0003328 A1  Jan. 6, 2005

Related U.S. Application Data

(63) Continuation-in-part of application No. 10/164,512, filed on Jun. 6, 2002, now Pat. No. 7,086,864, which is a continuation-in-part of application No. 09/684,493, filed on Oct. 6, 2000, now Pat. No. 6,428,319, which is a continuation-in-part of application No. 09/571,040, filed on May 12, 2000, now Pat. No. 6,447,297.

(60) Provisional application No. 60/133,733, filed on May 12, 1999.

(51) Int. Cl.
*A61C 5/02* (2006.01)

(52) U.S. Cl. .................................... 433/224
(58) Field of Classification Search .............. 433/81, 433/102, 221, 224
See application file for complete search history.

(56) References Cited

U.S. PATENT DOCUMENTS 277,943 A  5/1883  Richmond (Continued)

FOREIGN PATENT DOCUMENTS

DE  34 08 503 A1  9/1984

(Continued)

OTHER PUBLICATIONS

PCT International Search Report, Aug. 17, 2000.

(Continued)

*Primary Examiner*—Cary E. O'Connor
(74) *Attorney, Agent, or Firm*—Ann M. Knab

(57) ABSTRACT

An endodontic post comprises a combined endodontic post and tip of filling material such as thermoplastic material in a single unit. Obuturating systems are provided by an endodontic carrier and attached filling material. The post and obturator include a protrusion or depression on the tip section of the device for better attachment of the filling material to the device. Alternatively the post and obuturator are fabricated of a tube having a tunnel extending therethrough into which filling material is injected. The filling material extends out of the apical section of the post and obturator to form a filler cone.

54 Claims, 12 Drawing Sheets

U.S. PATENT DOCUMENTS

| | | |
|---|---|---|
| 674,419 A | 5/1901 | Kinsman |
| 1,312,120 A | 8/1919 | Hurtt |
| 1,463,963 A | 8/1923 | Miller |
| 1,469,992 A | 10/1923 | Card |
| 1,641,844 A | 9/1927 | Fisher |
| 1,649,508 A | 11/1927 | Carmichael |
| 3,066,112 A | 11/1962 | Bowen |
| 3,179,623 A | 4/1965 | Bowen |
| 3,194,784 A | 7/1965 | Bowen |
| 3,318,000 A | 5/1967 | Paris |
| 3,504,438 A | 4/1970 | Wittman et al. |
| 3,740,851 A | 6/1973 | Weissman |
| 3,751,399 A | 8/1973 | Lee, Jr. et al. |
| 3,813,779 A | 6/1974 | Tostl |
| 3,855,702 A | 12/1974 | Malmin |
| 3,899,830 A | 8/1975 | Malmin |
| 3,919,774 A | 11/1975 | Fishman |
| 3,926,906 A | 12/1975 | Lee, II et al. |
| 3,949,479 A | 4/1976 | Malmin |
| 3,968,567 A | 7/1976 | Nevins |
| 4,050,156 A | 9/1977 | Chasanoff et al. |
| 4,253,829 A | 3/1981 | Adelberger |
| 4,253,835 A | 3/1981 | Ware |
| 4,343,608 A | 8/1982 | Hodosh |
| 4,407,675 A | 10/1983 | Hodosh |
| 4,425,094 A | 1/1984 | Tateosian et al. |
| 4,480,996 A | 11/1984 | Crovatto |
| 4,480,998 A | 11/1984 | Carse |
| 4,505,675 A | 3/1985 | Albert |
| 4,505,676 A | 3/1985 | Gonser |
| 4,518,356 A | 5/1985 | Green |
| 4,525,147 A | 6/1985 | Pitz |
| 4,538,989 A | 9/1985 | Apairo, Jr. et al. |
| 4,543,065 A | 9/1985 | Bushway |
| 4,544,359 A | 10/1985 | Waknine |
| 4,547,531 A | 10/1985 | Waknine |
| 4,622,012 A | 11/1986 | Smoler |
| 4,657,592 A | 4/1987 | Takubo |
| 4,681,545 A | 7/1987 | Lapcevic |
| 4,682,949 A | 7/1987 | Warrin |
| 4,684,555 A | 8/1987 | Neumeyer |
| 4,717,341 A | 1/1988 | Goldberg et al. |
| 4,721,735 A | 1/1988 | Bennett et al. |
| 4,738,616 A | 4/1988 | Reynaud |
| 4,740,245 A | 4/1988 | Futami et al. |
| 4,746,292 A | 5/1988 | Johnson |
| 4,758,156 A | 7/1988 | Johnson |
| 4,766,200 A | 8/1988 | Riazi |
| 4,801,528 A | 1/1989 | Bennett |
| 4,813,876 A | 3/1989 | Wang |
| 4,820,152 A | 4/1989 | Warrin et al. |
| 4,846,685 A * | 7/1989 | Martin ........................ 433/221 |
| 4,871,312 A | 10/1989 | Heath |
| 4,882,407 A | 11/1989 | Riazi |
| 4,894,011 A | 1/1990 | Johnson |
| 4,894,012 A | 1/1990 | Goldberg et al. |
| 4,931,096 A | 6/1990 | Fujisawa et al. |
| 4,934,934 A | 6/1990 | Arpaio, Jr. et al. |
| 4,936,775 A | 6/1990 | Bennett |
| 4,936,776 A | 6/1990 | Kwiatkowski |
| 4,950,697 A | 8/1990 | Chang et al. |
| 4,952,150 A | 8/1990 | Schiwiora et al. |
| 4,966,952 A | 10/1990 | Riaza |
| 4,986,754 A | 1/1991 | Chang et al. |
| 5,051,093 A | 9/1991 | Fitzmorris |
| 5,064,373 A | 11/1991 | Staubli et al. |
| 5,067,900 A | 11/1991 | McSpadden |
| 5,073,112 A | 12/1991 | Weil |
| 5,074,792 A | 12/1991 | Bernadat |
| 5,083,923 A | 1/1992 | McSpadden |
| 5,085,586 A | 2/1992 | Johnson |
| 5,088,183 A | 2/1992 | Lee |
| 5,088,927 A | 2/1992 | Lee |
| 5,089,183 A | 2/1992 | Johnson |
| 5,092,773 A | 3/1992 | Levy |
| 5,098,298 A | 3/1992 | Johnson |
| 5,104,321 A | 4/1992 | Filhol |
| 5,106,298 A | 4/1992 | Heath et al. |
| 5,118,297 A | 6/1992 | Johnson |
| 5,149,268 A | 9/1992 | Johnson |
| 5,161,973 A | 11/1992 | Johnson |
| 5,165,893 A | 11/1992 | Thompson |
| 5,171,146 A | 12/1992 | Guerci |
| 5,181,850 A | 1/1993 | Neumeyer |
| 5,190,702 A | 3/1993 | Johnson |
| 5,215,461 A | 6/1993 | Riazi |
| 5,232,440 A | 8/1993 | Wilk |
| RE34,439 E | 11/1993 | Heath |
| 5,275,562 A | 1/1994 | McSpadden |
| 5,276,068 A | 1/1994 | Waknine |
| 5,286,193 A | 2/1994 | Roane |
| 5,286,423 A | 2/1994 | Johnson |
| 5,302,129 A | 4/1994 | Heath et al. |
| 5,326,263 A | 7/1994 | Weissman |
| 5,328,367 A | 7/1994 | Johnson |
| 5,328,372 A | 7/1994 | Reynaud et al. |
| 5,372,759 A | 12/1994 | Johnson |
| 5,380,200 A | 1/1995 | Heath et al. |
| 5,382,161 A | 1/1995 | Roane |
| 5,395,240 A | 3/1995 | Paschke et al. |
| 5,409,378 A | 4/1995 | Pohl |
| 5,415,547 A | 5/1995 | Torabinejad et al. |
| RE35,070 E | 10/1995 | Fitzmorris |
| 5,464,362 A | 11/1995 | Heath et al. |
| 5,518,399 A | 5/1996 | Sicurelli, Jr. et al. |
| RE35,264 E | 6/1996 | Bennett |
| 5,527,205 A | 6/1996 | Heath et al. |
| 5,540,766 A | 7/1996 | Castellani |
| 5,564,929 A | 10/1996 | Alpert |
| 5,588,835 A | 12/1996 | Kert |
| 5,595,486 A | 1/1997 | Manocha |
| 5,605,460 A | 2/1997 | Heath et al. |
| 5,624,259 A | 4/1997 | Heath et al. |
| 5,624,976 A | 4/1997 | Klee |
| 5,628,674 A | 5/1997 | Heath et al. |
| 5,648,403 A | 7/1997 | Martin |
| 5,653,590 A | 8/1997 | Heath et al. |
| 5,655,950 A | 8/1997 | Heath et al. |
| 5,713,736 A | 2/1998 | Heath et al. |
| 5,741,139 A | 4/1998 | Sicurelli, Jr. et al. |
| 5,752,825 A | 5/1998 | Buchanan |
| 5,756,559 A | 5/1998 | Blackwell et al. |
| 5,762,497 A | 6/1998 | Heath |
| 5,762,541 A | 6/1998 | Heath et al. |
| 5,769,638 A | 6/1998 | Torabinejad et al. |
| 5,797,748 A | 8/1998 | Reynaud et al. |
| 5,803,736 A | 9/1998 | Merritt, Jr. |
| 5,807,106 A | 9/1998 | Heath |
| 5,816,816 A | 10/1998 | Scharf |
| 5,833,457 A | 11/1998 | Johnson |
| 5,833,464 A | 11/1998 | Foser |
| 5,882,196 A | 3/1999 | Kert |
| 5,915,970 A | 6/1999 | Sicurelli, Jr. et al. |
| 5,919,044 A | 7/1999 | Sicurelli, Jr. et al. |
| 5,921,775 A | 7/1999 | Buchanan |
| 5,925,179 A | 7/1999 | Mannschedel |
| 5,941,760 A | 8/1999 | Heath et al. |
| 5,948,129 A | 9/1999 | Nonami et al. |
| 5,989,032 A | 11/1999 | Reynaud et al. |
| 6,010,335 A | 1/2000 | Kert |
| 6,012,924 A | 1/2000 | Reynaud et al. |
| 6,024,565 A | 2/2000 | Sicurelli et al. |
| 6,024,569 A | 2/2000 | Ohne et al. |

| | | | |
|---|---|---|---|
| 6,028,125 A | 2/2000 | Combe et al. | |
| 6,030,220 A | 2/2000 | Karmaker et al. | |
| 6,039,569 A | 3/2000 | Prasad et al. | |
| 6,074,209 A | 6/2000 | Johnson | |
| 6,106,296 A | 8/2000 | Johnson | |
| 6,120,294 A | 9/2000 | Engelbrecht et al. | |
| 6,126,446 A | 10/2000 | Mannschedel | |
| 6,162,056 A | 12/2000 | Mannschedel | |
| 6,183,253 B1 | 2/2001 | Billet et al. | |
| 6,186,791 B1 | 2/2001 | Karmaker et al. | |
| 6,214,048 B1 | 4/2001 | Ito et al. | |
| 6,220,863 B1 | 4/2001 | Kamohara et al. | |
| 6,224,377 B1 | 5/2001 | Lieland et al. | |
| 6,254,392 B1 | 7/2001 | Mannschedel et al. | |
| 6,261,099 B1 | 7/2001 | Senia et al. | |
| 6,264,471 B1 | 7/2001 | Martin | |
| 6,267,597 B1 | 7/2001 | Kim | |
| 6,287,122 B1 | 9/2001 | Seeram et al. | |
| 6,293,795 B1 | 9/2001 | Johnson | |
| 6,371,763 B1 | 4/2002 | Sicurelli, Jr. et al. | |
| 6,428,319 B1 | 8/2002 | Lopez et al. | |
| 6,447,297 B1 | 9/2002 | Lopez et al. | |
| 6,455,608 B1 | 9/2002 | Jia et al. | |
| 6,461,420 B2 | 10/2002 | Ikuta | |
| 6,472,454 B1 | 10/2002 | Qian | |
| 6,537,563 B2 | 3/2003 | Jia et al. | |
| 6,566,418 B2 | 5/2003 | Imai et al. | |
| 6,568,937 B2 | 5/2003 | Kamohara et al. | |
| 6,787,584 B2 | 9/2004 | Jia et al. | |
| 2002/0072035 A1 | 6/2002 | Hickok | |
| 2002/0142261 A1 | 10/2002 | Van Den Houdt | |
| 2002/0147249 A1 | 10/2002 | Klee et al. | |
| 2002/0198283 A1 | 12/2002 | Imal et al. | |
| 2003/0045604 A1 | 3/2003 | Klee | |
| 2003/0113686 A1 | 6/2003 | Jla et al. | |
| 2003/0124483 A1 | 7/2003 | Jia et al. | |
| 2003/0207960 A1 | 11/2003 | Jia | |
| 2004/0115589 A1 | 6/2004 | Karmaker et al. | |
| 2004/0248067 A1 | 12/2004 | Lopez et al. | |
| 2004/0249015 A1 | 12/2004 | Jia et al. | |
| 2004/0265783 A1 | 12/2004 | Karmaker et al. | |
| 2005/0066854 A1 | 3/2005 | Jia et al. | |
| 2005/0069836 A1 | 3/2005 | Jia et al. | |

FOREIGN PATENT DOCUMENTS

| | | |
|---|---|---|
| DE | 35 04 472 A1 | 7/1986 |
| DE | 35 12 938 A1 | 10/1986 |
| DE | 35 13 864 A1 | 10/1986 |
| DE | 38 39 466 C2 | 6/1989 |
| DE | 41 03 355 A1 | 6/1992 |
| EP | 0 539 751 A1 | 5/1993 |
| FR | 557.756 | 5/1923 |
| FR | 1.180.326 | 7/1957 |
| FR | 2 616 653 | 6/1987 |
| FR | 2 669 211 | 5/1992 |
| FR | 2 730 627 | 8/1996 |
| GB | 1 412 077 | 10/1975 |
| WO | WO 93/14714 | 8/1993 |
| WO | WO 93/19687 | 10/1993 |
| WO | WO 98/11842 | 3/1998 |
| WO | WO 00/67659 | 11/2000 |
| WO | WO 02/078646 | 10/2002 |
| WO | WO 2004/037214 A1 | 5/2004 |

OTHER PUBLICATIONS

International Preliminary Examination Report, Oct. 4, 2001.
Dentsply Product Information "Densfil" [http://www.mailefer.com/html/obturation.html]. May 2001.
Dentsply Product Information "Thermasystem Plus Obturation System" [http:/www.xray.essix.com/endodontics/endomain.html]. May 2001.
Softcore Dental Products Product Information "Softcore" [http://www.variodent.at/grossha/022000/soft-core.htm]. May 2001.
PCT Written Opinion with date of mailing Jan. 26, 2001.
Notification of Transmittal of the International Preliminary Examination Report with date of mailing Jan. 24, 2005.
PCT Notification of Transmittal of the International Search Report and the Written Opinion of theInternational Searching Authority, or the Declaration with date of mailing Apr. 1, 2005.
PCT International Search Report with date of mailing Nov. 6, 2003.
PCT Written Opinion with date of mailing Jun. 15, 2004.
PCT Written Opinion with date of mailing Nov. 5. 2004.
Product Information for TONE P757 Polymer, Form No. 321.00050, Dow Chemical Company, Dec. 2001.
Product Information for TONE P767 Polymer, Form No. 321-00051, Dow Chemical Company, Dec. 2001.
Product Information for TONE P787, Polymer, Form No. 321-00052, Dow Chemical company, Dec. 2001.
Shipper G., Orstavik D., Teixeira FB., Trope M., An Evaluation of Microbial Leakage in Roots Filled with a Thermoplastic Synthetic Polymer-Based Root Canal Filling Material(Resilon), Jurnal of Endodontics, vol. 30, No. 5, May 2004, pp. 342-347.
Teixeira FB., Teixeira ECN, Thompson JY, Trope M., "Fracture Resistance of Roots Endodontically Treated with a New Resin Filling Material", JADA 2004; 135:646-652.
Nahmias Y., Serota KS, Watson, Jr. WR, "Predictcable Endodontic Success: Part II-Microstructural Replication", Oral Health Journal, Dec. 2003.
Mounce R, Glassman G, "Bonded Endodontic Obturation: Another Quantum Leap Forward for Endodontics", Oral Health Journal, Jul. 2004.
Chivian N, "Resilon - The Missing Link in Sealing the Root Canal", Compenduim, vol. 25, No. 10A, Oct. 2004, pp. 823-825.
Shipper G, Teixeira FB, Arnold RR, Trope M, "perlapical Inflammation after Coronal Microbial Innoculation of Dog Roots Filled with Gutta-Percha or Resilon", Jurnal of Endodontics, vol. 31, No. 2, Feb. 2005, pp. 91-96.
Barnett F, Trope M, Adhesive Endodontics: Combining Technologies for Enhanced Success:, Dentaltown, vol. 5, Issue 8, Aug. 2004, pp. 34-38.
Goff S, "Easier Endo, A DPR survey report", Dental Products Report, Sep. 2004, pp. 14-20.

* cited by examiner

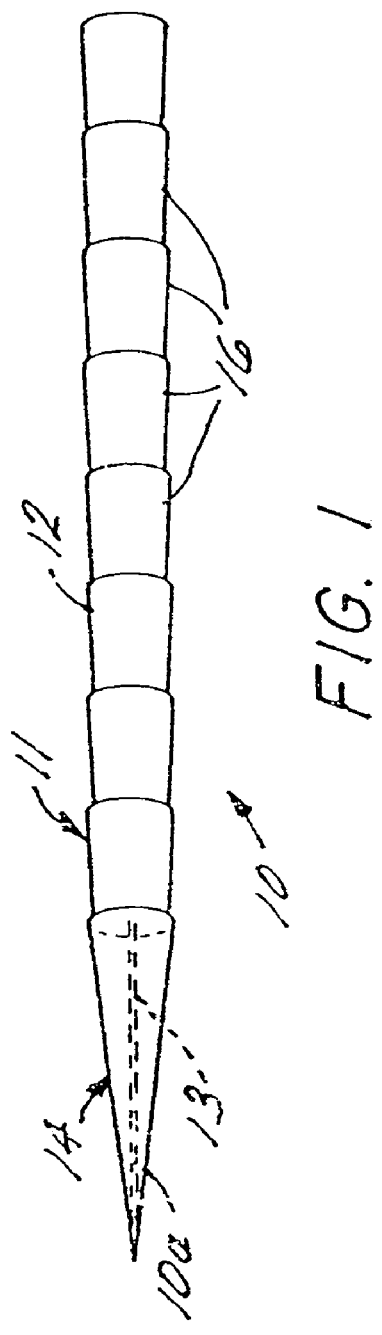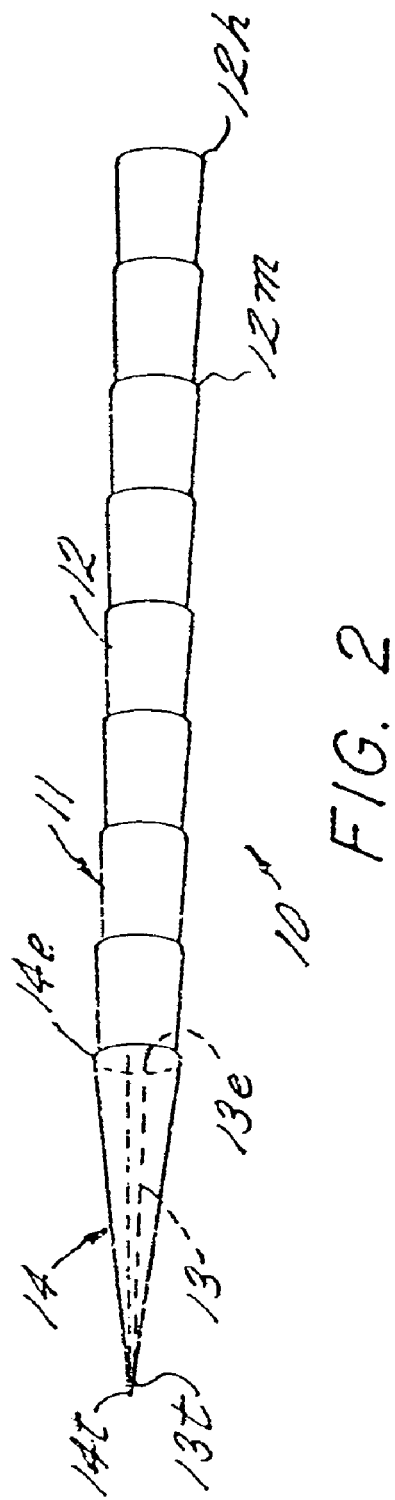

ENDODONTIC POST AND OBTURATING SYSTEM

CROSS-REFERENCE TO RELATED APPLICATIONS

This application is a continuation-in-part application of U.S. patent application Ser. No. 10/164,512, filed Jun. 6, 2002, now U.S. Pat. No. 7,086,864 which is a continuation-in-part of U.S. patent application Ser. No. 09/684,493, filed Oct. 6, 2000, now U.S. Pat. No. 6,428,319 which is a continuation-in-part of U.S. patent application Ser. No. 09/571,040, filed May 12, 2000, now U.S. Pat. No. 6,447,297 which claims priority to U.S. Provisional Application No. 60/133,733, filed May 12, 1999, which are all incorporated herein by reference.

FIELD OF THE INVENTION

This invention relates to both the obturation of a root canal having undergone endodontic treatment and the simultaneous placement of an endodontic post system or filling material.

BACKGROUND OF THE INVENTION

Endodontics or root canal therapy is that branch of dentistry that deals with the diseases of the dental pulp and associated tissues. One aspect of endodontics comprises the treatment of infected root canals, the removal of diseased pulp tissues, followed by the biomechanical modification and the subsequent filling of the pulp canal (root canal). Root canal therapy is generally indicated for teeth having sound external structures but having diseased, dead or dying pulp tissues. Such teeth may or may not generally possess intact enamel and dentin and are satisfactorily engaged with bony tissue. In such teeth, the pulp tissue and excised portions of the root should be replaced by a biocompatible substitute.

One technique for the preparation of a root canal involves creating a coronal access opening with a conventional dental drill. A tool is used for gross removal of pulp material from the root canal through the coronal access opening. The void formed is enlarged with reamers and/or files to result in a fully excavated cavity. Debris is removed from this cavity by flushing and the cavity is cleansed to remove all diseased tissue. Following chemical antisepsis, the excavated canal is ready for filling.

A basic method involves inserting a filling cone into a root canal and cementing therein to obturate the canal. Lateral condensation is a method in which several filling cones, a primary cone and auxiliary cones, are inserted into a root canal. The primary cone is inserted and cemented to the seat of the root canal. Using a tapered spreader, the primary cone is then squeezed against the side of the root canal and a second cone is inserted and cemented into place. This process is continued until the root canal is completely obturated which can require up to 10 to 15 filling cones. Vertical condensation of warm or hot gutta percha is yet another method of sealing root canals. After cementing a primary cone short of the apex of the root canal, heat application is alternated with a series of smaller and smaller pluggers until the gutta percha is moved to the apex. This is often possible when the smallest plugger approaches the apex of the tooth within 3 to 5 millimeters. The space is then backfilled. Lateral canals are packed and sealed as a consequence of lateral expansion of a wave of heated gutta percha. Alternatively, small segments of gutta percha can be used in this method that are inserted into the root canal, heated in order they can adhere to one another and each backfilled one at a time until the root canal is filled. All three of these methods, the single filling cone, lateral condensation and vertical condensation apply root canal cement or sealer around the individual cones or in between segments as a binding agent.

Another method employs an injection gun that injects warm or hot gutta percha filling material into a root canal. The injector initially places heated gutta percha at the seat of the root canal which is then condensed with a plugger into the root tip. The injector then backfills the root canal by injecting additional gutta percha into the root canal until it is obturated. A similar method involves heating gutta percha on a flexible metal carrier used to insert the gutta percha into the root canal. The carrier may be a solid rod, or a hollow rod, situated in the center of a master cone. The rod is connected to a handle which may be removed by slipping it out of the hollow rod, or cutting it off if it is a solid rod. While these systems provide for convenient and quick obturation of the canal, they pose a removal problem for the dentist who has to place a post.

Of all the methods used for obturating a canal, there is no device currently available that will allow a doctor to simultaneously obturate a root canal and place an endodontic post. Currently, an endodontist will perform the root canal procedure and the obturation during one patient visit. After the canal is obturated and temporarily sealed, the patient is frequently treated by a second dentist who will place the post. To do so, the gutta percha has to be removed from the canal until only a portion 5 mm or so from the apex remains to act as an apical seal. The rods inside the current systems make gutta percha removal much more difficult since the coronal portion of the gutta percha rod has to be removed to allow for the placement of the endodontic post. One way to overcome this problem has been to notch the obturating rod with a bur. Then, when the obturator is placed in the canal it is twisted, snapping off the apical portion. The longer coronal portion is removed. It is then re-introduced into the canal and the gutta percha is stripped off by means of pulling the rod through an endodontic stop. Since the endodontic stop is extremely narrow, the gutta percha is pulled from the rod as it is withdrawn and the gutta percha remains in the canal. It is subsequently condensed. As a result of this technique, the restoring dentist does not have to deal with the rod and only has to remove the gutta percha to make room for the post. Some gutta percha may remain on the walls of the canal jeopardizing the bond strength of the post the radicular dentin. Reinfection of the treated tooth can be a problem because the endodontist performing the root canal procedure will seal the coronal opening with a temporary stopping agent which can leak oral fluids carrying bacterial into the canal opening.

It is desirable to reduce the steps and time involved in performing obturation and placement of a post in a root canal. It would be beneficial to limit the obturation and post placement to a single visit to the dentist or prosthodontist. It is advantageous to reduce and/or eliminate the leakage problems associated with poor sealing at the coronal end of the canal.

SUMMARY OF THE INVENTION

These and other objects and advantages are accomplished by the endodontic post of the present invention comprising a combined endodontic post and tip of filling material such as thermoplastic material in a single unit. Obuturating systems are provided by an endodontic carrier and attached filling material. To use the post unit, the tip of the device may be softened by placing in an oven or heater to heat and soften the filling material or chemically treating to soften the material. The device will then be placed in a root canal that has been opened to a predetermined dimension by use of endodontic files, to seal the apical end. If necessary, the gutta percha can be compacted toward the apex, while it is still in the softened state, to ensure the apex is adequately sealed. The post may then be cemented into place by lining the canal walls with a bonding agent and filling the interface between the post and the walls of the canal with a resin cement such as a dual cure cement, a light cure cement or a self cure cement such as Lute-It® dual cure luting cement or Cement-It® Universal cement, both available from Pentron Clinical Technologies, LLC, in Wallingford, Conn. This will result in a coronal seal of the canal via resin restorative material and an apical seal of the canal by means of gutta percha and sealant. The remaining portion of the post, extending supragingivally, will be used to build a core around it. Any excess will be cut off. One length of the device will be longer to accommodate the longer roots in anterior teeth. Another length will be shorter to accommodate smaller roots in the molar region. Various diameters may also be provided to accommodate the different sizes of root canals. The bonded flexible post may strengthen the tooth to prevent subsequent root fractures.

In another embodiment herein, the post and obturator include a protrusion or depression on the tip section of the device for better attachment of the filling material to the device.

In yet another embodiment, the post and obturator are fabricated of a shaft or carrier having an opening extending therethrough into which filling material is injected. The filling material extends out of the apical section of the post and obturator to form a filler cone.

BRIEF DESCRIPTION OF THE DRAWINGS

Features of the present invention are disclosed in the accompanying drawings, wherein similar reference characters denote similar elements throughout the several views, and wherein:

FIG. 1 is an elevational view of a post in accordance with the invention;

FIG. 2 is an elevational view of a post with an alternate carrier in accordance with the invention;

DESCRIPTION OF THE INVENTION

Figure 3:
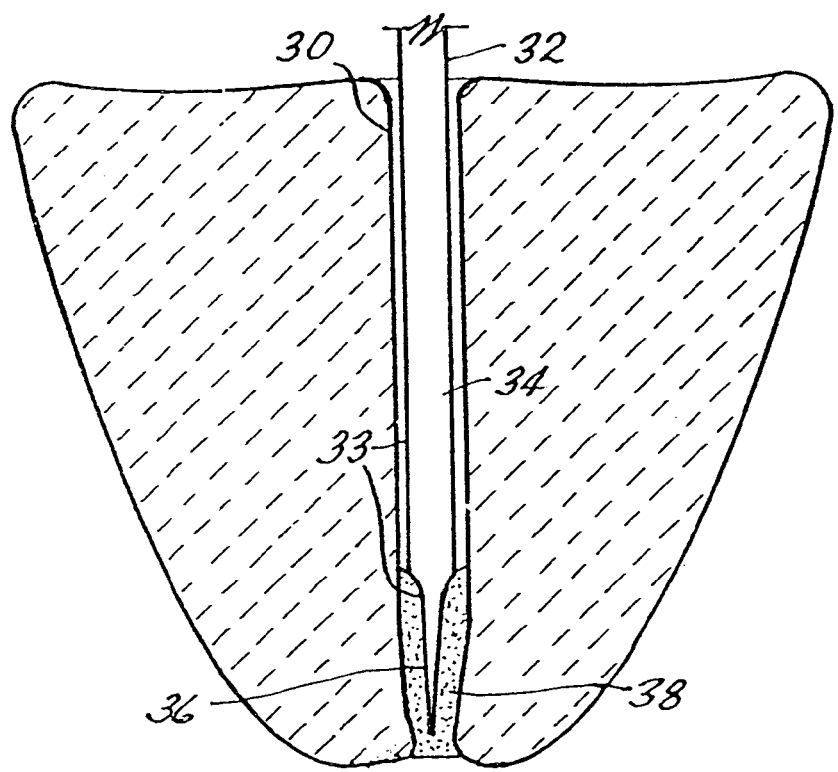
FIG. 3 is a sectional view of a tooth showing a post of the invention placed in the root canal.

As will be appreciated, the present invention provides a combination endodontic post and filler cone in a single unit. Reference is made to FIGS. 1 and 2 which show a post unit 10 comprising a post section 11 and a cone or tip section 14. Tip section 14 comprises a flexible rod or cone of biocompatible material for filling the apex of the canal. The filling material is typically a thermoplastic, chemo-plastic (i.e., may be softened by chemicals), resinous or similar polymeric material, such as gutta percha and is attached to post section 11 at the apical end 10a. Other examples of thermoplastic materials include but are not limited to HEMA methacrylate, polyurethane, polypropylene and polyethylene.

Additional examples of thermoplastic materials include polyacrylate, polyamide, fluoropolymer, polyester, polyphosphazene, polyanhydride, polysulfide, polyether, epoxy, polycarbonate, polystyrene, polybutadiene, polyphenylene oxide, silicone rubber, polylactides, polyglycolides, polycaprolactones, polyanhydrides, polyamides, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyethylene oxides, polyacrylates/methacrylates, polyalkylene succinates, poly(malic acid) polymers, polymaleic anhydrides, poly(methylvinyl) ethers, poly(amino acids), chitin, chitosan, and copolymers, terpolymers, and combinations or mixtures thereof. Examples of polyacrylates include polymethyl methacrylate, polyhydroxy ethyl methacrylate, and hydroxy ethyl methacrylate (HEMA). Examples of fluoropolymers include Teflon® PTFE and Teflon® PFA. Examples of polyesters include polylactic acid, glycolide, polycaprolactone and co-polymers thereof. Examples of silicone rubber include polysiloxane.

The filling material may include additives typical in the dental field such as plasticizing, antibiotic, cariostatic, antibacterial, or other anti-inflammatory, biologically active or therapeutic materials.

Post section 11 comprises a main body or endodontic portion 12 and a carrier or apical portion 13 which is located at the apical end 10a of post unit 10. Main body 12 may be a solid rod of circular or other suitable cross-section comprising a substantially smooth surface or may comprise a plurality of frustoconical sections 16 arranged coaxially along the longitudinal axis of main body 12. Preferably, main body 12 has consistent width along the longitudinal axis thereof whereas frustoconical sections 16 each have the same tapered width and same length. It is possible to vary the width and/or length of main body 12 and/or vary the tapered width and/or length of frustoconical sections 16 along the longitudinal axis of main body 12. Main body 12 may include a larger head of any shape with or without a retentive design to provide support for a core thereon at the supracoronal end 12h as will be discussed hereinafter.

Carrier 13 is preferably an extension of main body 12 of post section 11 and is of very fine diameter to accommodate tip section 14 of thermoplastic material of post unit 10. In one method of manufacture which will be discussed hereinafter, post section 11 is manufactured from a rod of material that is cut or machined at the apical end 10a to result in carrier 13 having a very small width or diameter in comparison to main body 12. Carrier 13 is of small diameter to allow enough area to form tip section 14 thereon, and also of enough strength and integrity to accommodate the filling material such as a thermoplastic material. As stated above, carrier 13 is preferably an extension of main body 12 and is shown having constant diameter along the length thereof, but may be of any shape or size sufficient to hold tip section 14 thereon. FIG. 2 shows an alternative carrier 13 of tapered diameter.

Post section 11 may be fabricated of any material to provide a flexible apical portion and a more rigid endodontic and/or coronal or supracoronal portion, such as metal, plastic, ceramic, polymeric, composite, or other material suitable for placement in the mouth. Composite materials include but are not limited to filler reinforced composite materials and fiber reinforced composite materials comprising the reinforcing component in a polymeric matrix material such as those composite materials listed in U.S. Pat. Nos. 4,717,341 and 4,894,012 to Goldberg et al., U.S. Pat. No. 6,039,569 to Prasad et al., U.S. Pat. No. 6,030,220 to Karmaker et al, U.S. Pat. No. 5,564,929 to Alpert, and U.S. Pat. No. 5,919,044 to Sicurelli, Jr. et al., all of which are hereby incorporated by reference. The fiber reinforced composite material may comprise fibers in the form of long, unidirectional, continuous filaments which are preferably at least partially aligned and oriented along the longitudinal dimension of the component with alignment normal or perpendicular to that dimension also possible. The fibers may be of uniform or random length, unidirectional or multidirectional, or randomly dispersed, and may be as short as about 3 to about 4 millimeters (mm) or shorter. The fibers may also be in the form of fabric as set forth in copending Ser. No. 09/280,760 filed Mar. 29, 1999 and may include any of the attributes of the post described therein, the contents all of which are hereby incorporated by reference. Due to the improved structural integrity, the amount of fibers in the structural component preferably equals at least about 20% by weight (wt %) and preferably about 20 wt % to about 70 wt %. Possible reinforcing fibers, which are preferably used in accordance with U.S. Pat. Nos. 4,717,341 and 4,894,012 to Goldberg et al. (which are herein incorporated by reference), include glass, ceramic, metal, carbon, graphite, polymeric such as cellulose, polyamide, aramid, polyester, polyaramid, acrylic, vinyl and modacrylic, polyolefin, polytetrafluorethylene, mixtures thereof, as well as other fibers known in the art. One preferred version of the device is comprised of unidirectional microfilamentous glass fibers bundled in a resin matrix.

In order to enhance the bond between the fibers and polymeric matrix, thereby enhancing the reinforcing effect, the fibers may be silanized or otherwise treated such as by grafting functional monomers or by surface modification by corona, high voltage flame or plasma treatment, to obtain proper coupling between the fibers and the resin matrix. Silanization renders the fibers hydrophobic, reducing the water sorption and improving the hydrolytic stability of the composite material, renders the fibers organophilic, improving wetting and mixing, and bonds the fibers to the polymeric matrix. Typical silane is A-174 (p-methacrylate propyl tri-methoxy silane), produced by OSI Specialties, New York.

The polymeric matrix is selected from those known in the art of dental materials, including, but not limited to, polyamides, polyester, polyolefins, polyimides, polyarylates, polyurethanes, vinyl esters or epoxy-based materials, styrenes, styrene acrylonitriles, ABS polymers, polysulfones, polyacetals, polycarbonates, polyphenylene sulfides, polyarylsulfides, acrylonitrile-butadiene-styrene copolymers, polyurethane dimethacrylates (hereinafter abbreviated to PUDMA), and the like. Preferred polymeric matrix materials include those based on acrylic and methacrylic monomers, for example those disclosed in U.S. Pat. Nos. 3,066,112, 3,179,623, and 3,194,784 to Bowen; U.S. Pat. Nos. 3,751,399 and 3,926,906 to Lee et al.; and commonly assigned U.S. Pat. No. 5,276,068 to Waknine (which are herein incorporated by reference). An especially preferred methacrylate monomer is the condensation product of bisphenol A and glycidyl methacrylate, 2,2'-bis [4-(3-methacryloxy-2-hydroxy propoxy)-phenyl]-propane (hereinafter abbreviated "BIS-GMA").

The polymer matrix, which typically includes polymerization initiators, polymerization accelerators, ultra-violet light absorbers, anti-oxidants, fluorescent whitening agents, free radical initiators, and/or other additives well known in the art, may be visible light curable, self-curing, dual curing, or vacuum, heat, or pressure curable compositions, as well as any combination thereof. Heat and pressure or vacuum curable compositions include a heat cure initiator such as benzoyl peroxide, 1,1'-azobis(cyclohexanecarbo-nitrile) or other free radical initiators. The preferred polymeric matrix is a light and heat curable matrix, wherein light effects partial cure of the polymer matrix, while final curing is by heat under controlled atmosphere.

Fillers may be present in addition to or instead of fibers in an amount up to about 80 wt %, and preferably about 70 wt %. If fibers are present, the amount of filler is present in an amount of up to about 30 wt % of one or more fillers known in the art and used in dental restorative materials. Suitable fillers include those capable of being covalently bonded to the polymeric matrix itself or to a coupling agent that is covalently bonded to both. Fillers include silica, silicate glass, quartz, barium silicate, strontium silicate, barium borosilicate, strontium borosilicate, borosilicate, lithium silicate, amorphous silica, ammoniated or deammoniated calcium phosphate and alumina, zirconia, tin oxide, and titania, among other conventional fillers such as those disclosed in commonly assigned U.S. Pat. Nos. 4,544,359 and 4,547,531 to Waknine (which are incorporated herein by reference), while possible coupling agents include silanes, zirconates, and titanates. If the post is manufactured from a composite material, it is preferably in completely cured or hardened state. However, some uncured residual monomers may be still present in the hardened post.

Examples of metals useful as post section 11 include but are not limited to metals or alloys of Pd, Pt, Rh, Ir, Au, Ag, Ti, Co, Mo and mixtures thereof such as AgPd, AuPtPd, TiAlFe, TiAlV, CoCrMo, stainless steel and brass. Ceramic materials useful in the fabrication of post section 11 include but are not limited to alumina, zirconia, mullite, spinel, porcelain, titania, lithium disilicate, leucite, amorphous glass, lithium phosphate, and combinations thereof, or any high strength ceramic material which can withstand the stresses created in the mouth.

In accordance with one method of manufacture herein, post section 11 (which includes main body 12 and carrier 13) is manufactured by any known method in the art and depending upon the material used for the manufacture of post section 11. Such methods include but are not limited to matched die processes, autoclave molding, resin injection molding (RIM), sheet, dough and bulk molding, press molding, injection molding, reaction injection molding, resin transfer molding (RTM), compression molding, open molding, hand rolling, dipping and rolling, pressing, extrusion, pultrusion and filament winding. As discussed above, post section 11 is formed into a rod-shaped unit or main body 12 having a very fine or thin apical end or carrier 13. The final shape of post section 11 may be formed simultaneously during the manufacturing process thereof. Alternatively, a rod shaped material may be manufactured and thereafter shaped by grinding, cutting, milling or the like into the desired shape and size. As shown in FIGS. 1 and 2, post section 11 is a rod-shaped component having a main body 12 comprising slightly tapered stepped sections 16, all of the same dimensions and whereby one end of post section 11 comprises a very narrow section, 13, which acts as the carrier for the filling material. As with sections 16, carrier 13 may be formed during the actual manufacture of main body 12 or thereafter by grinding, cutting or similar means. Although main body 12 includes sections 16 to aid in the retention of the post in the canal, main body 12 may be of any surface (e.g., smooth, partly smooth, partly frustoconical, longitudinal or circular grooves) and shape suitable for placement in the canal such as in the case of smaller diameter posts whereby the ledges may be eliminated so as to maintain the structural integrity pi and strength of the post. Carrier 13 preferably comprises a smooth surface, although it is in no way limited to such and may be of any surface suitable for application of filling material thereon. The post may be provided in an opaque tooth color or it may be colored similar to a tooth's pulp for enhanced esthetics. The post may include an appropriate amount of raadiopaque material such as titanium oxide, bismuth oxychloride, barium sulfate, and similar materials known in the dental industry to insure x-ray documentation which may be added to the post material during manufacture thereof.

After post section 11 has been manufactured, carrier 13 of post section 11 is then coated with a filling material such as gutta percha to obtain cone section 14 thereon. The filling material may be applied by any known means such as dipping, injection molding, hand rolling, spraying, and the like. The filling material may be any suitable material used for filing root canals.

The length of post unit 10 may vary depending upon the length of the root into which it will be inserted. It is preferable that post 10 be manufactured in a variety of lengths and widths to fit the many different root canals of dental patients and the differing lengths of the anterior (central and lateral incisors, bicuspids and premolars) and molar teeth. Preferably, post unit 10 is about 14 to about 31 mm in length and more preferably about 16 to about 25 mm in length. For the length parameter, post section 11 may be divided into three sections. Section 13 is the apical section and is about 3 to about 15 mm in length and preferably about 5 to about 12 mm in length. If section 13 is tapered as in FIG. 2, the taper may be continuous at about 0.02 mm/per mm as per ISO standard or 0.04 mm/mm or 0.06 mm/mm from the apical tip 13t to the end 13e of carrier 13. As stated above, carrier 13 is covered with a filling material such as a thermoplastic material which does not extend more than a few mm in length past the tip of 13 (13t). Main body 12 comprises a main section from point 13e to point 12m which is about 10 to about 25 mm in length and preferably about 12 to about 16 mm in length, and a supracoronal portion or "head" of post section 11 from point 12m to point 12h which about 5 to about 15 mm and more preferably about 8 to about 10 mm in length. The supracoronal portion of post unit 11 will be used to build a core upon which a crown will be placed. The main section (from 13e to 12m) of main body 12 of post section 11 may be slightly flexible to negotiate curved canals.

The diameter of post section 11 will also vary and range from about 0.12 to about 0.25 mm at the apical end (13t–13e) and preferably from about 0.13 to about 0.20 at the apical end (13t–13e). If carrier 13 is tapered, the diameter at 13t is in the range of about 0.12 to about 0.25 mm and preferably about 0.13 to about 0.20 mm and the diameter at 13e is in the range of about 0.18 to about 0.30 and preferably about 0.20 to about 0.25 mm. At the supracoronal end, the diameter is about 0.4 to about 2.0 and preferably about 0.5 to about 1.75 mm.

Tip section 14 comprising the filling material is about 0.5 to 1 mm longer than carrier 13, but the diameter of tip section 14 is tapered from point 14e to point 14t in accordance with ISO standards to correspond to current obturating techniques utilizing master cones of thermoplastic material. Accordingly, tip section 14 can be tapered at least 0.02 mm/per mm in accordance with ISO standards, and preferably 0.02, 0.04 or 0.06 mm/per mm, or greater, measuring from tip 14t to 14e, for insertion into canals created with 0.02, 0.04., 0.06, or greater, tapered files. The diameter of tip 14 at point 14e is in the range of about 0.30 to about 2.0 mm and preferably 0.35 to about 1.5 mm. The diameter of tip 14 at point 14t is in the range of about 0.20 to about 1.0 mm and preferably about 0.25 to about 0.80 mm. When using the post unit in canals of 0.02 taper, the filling material such as thermoplastic material will be compressed by the canal and forced toward the coronal end of the canal. This will result in an apical seal in excess of 8 mm. The excess thermoplastic material can be removed with a heated instrument after it has hardened. When using the post unit in 0.06 tapered canals, the filling material can be condensed down toward the apex to fill the void created by the greater taper. This will result in an apical seal less than 8 mm, but in excess of 4 mm which is sufficient to maintain the apical seal.

To use the post unit, the device is placed in or near an oven or heater to heat and soften the filling material or dipped in a chemical solution such as chloroform to soften the filling material. Alternatively, the post is not heated or softened and is instead placed in its hardened state. The device will then be placed in a root canal that has been opened to a predetermined dimension by use of endodontic files, to seal the apical end. If necessary, the gutta percha can be compacted toward the apex, while it is still in the softened state, to ensure the apex is adequately sealed. The post is then cemented into place by lining the canal walls with a bonding agent and filling the interface between the post and the walls of the canal with a resin cement, such as a dual cure cement. This will result in a coronal seal of the canal via resin restorative material and an apical seal of the canal by means of gutta percha and sealant. The remaining portion of the post, extending supra-gingivally, will be used to build a core around it, and if necessary, for placement of a crown thereon. Any excess of the post will be cut off. One length of the device will be longer to accommodate the longer roots in anterior teeth. Another length will be shorter to accommodate smaller roots in the molar region.

FIG. 3 shows a root canal 30 with post unit 32 therein. Post unit 32 comprises a post section 33 having a main body 34 and a carrier 36 that carries the filling material 38. As shown in FIG. 3, the thermoplastic material 38 was softened prior to insertion and fills the apex of the canal.

Figure 4:
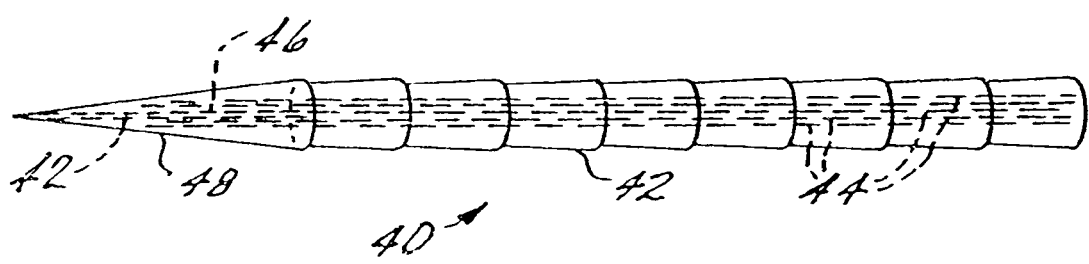
FIG. 4 is an elevational view of an alternate embodiment of a post in accordance with the invention.

In an alternate embodiment herein, reference is made to FIG. 4 wherein a post unit 40 comprises a post section 42 fabricated of fiber reinforced composite material wherein the fibers comprise optical fibers 44 such as glass fibers or a central core of a material such as metal which is able to transmit heat energy to the filling material. Glass fibers 44 extend out through post section 42 into carrier 46 and tip section 48. To use the post unit 40, the filling material 48 does not have to be softened or heated prior to insertion into the canal. Post unit 40 is inserted into the canal with tip 48 in its hardened state. A curing light or other heat source is applied to the coronal portion of the post, transmitting light or heat down toward the apex. Fibers 44 convert the light into heat or, alternatively, the core section transmits heat to the filling material. The heat then plasticizes the filling material such as gutta percha at the apex. The post is then pushed toward the apex using gentle finger pressure. This last step insures that the plasticized gutta percha is compressed apically and laterally, sealing the tooth and any lateral canals.

One of the benefits of this alternative embodiment is that it insures plasticized gutta percha is only introduced to the apical portion of the root and that the coronal portion of the root is free of gutta percha which could negatively affect the retentive strength of the post and core.

Figure 5:
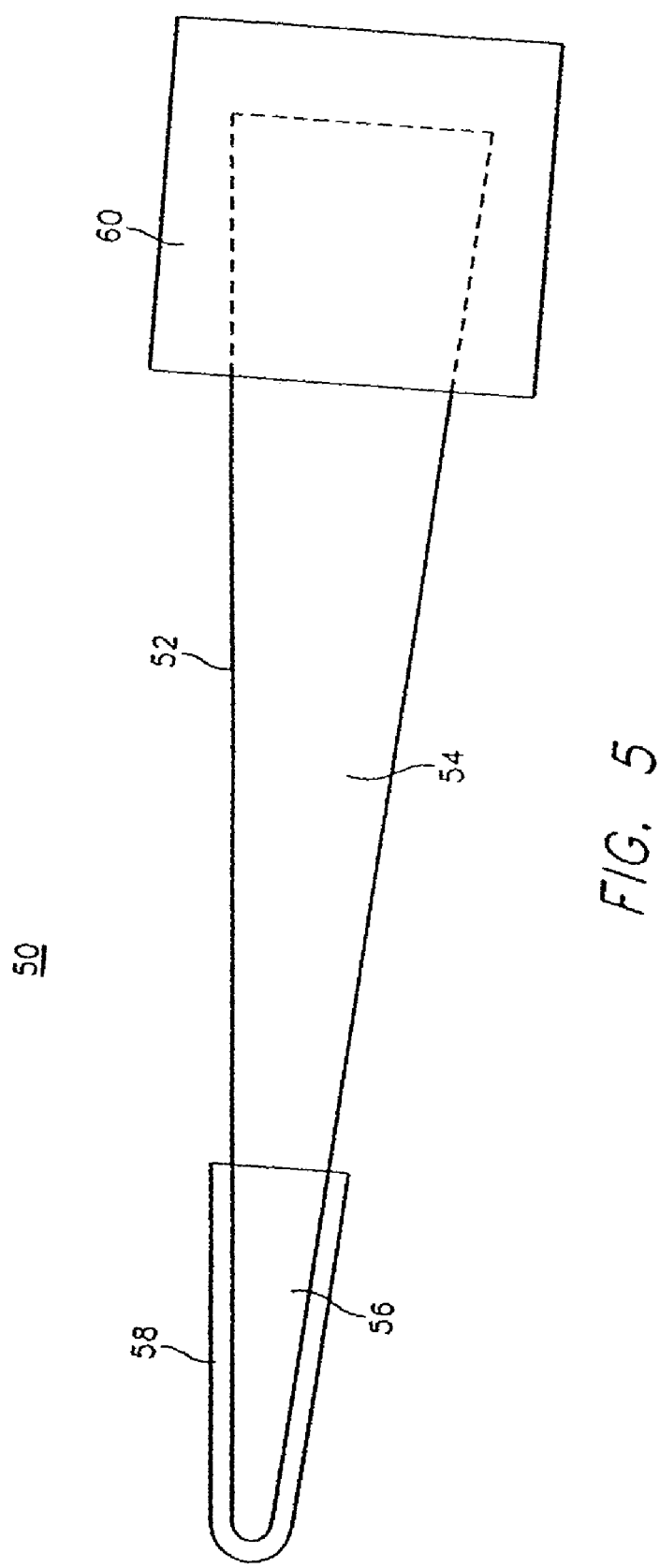
FIG. 5 is an elevational view of an alternate embodiment of a post in accordance with the invention.

In yet another embodiment herein, reference is made to FIG. 5 wherein a post unit 50 comprises a post section 52 fabricated of fiber reinforced composite material. Post section 52 includes main body 54 and carrier 56. Carrier 56 is coated with a filling material such as gutta percha to obtain cone section 58 thereon. As shown in the drawing, main body 54 is tapered to provide ease of placement into the canal. The cross-section of post unit 50 may be smaller than the cross-section of a standard post to fit in thinner or smaller auxiliary canals which are normally filled with a thermoplastic material. Accordingly, post unit 50 can act as an obturator. As an obturator, better support is provided due to the fiber-reinforced composite structural component 54 upon which cone section 58 is applied in comparison to using only a thermoplastic material as an obturator. Moreover, the obturator may be easily cemented in place in the canal. The size of post unit 50 is about 15 to about 35 mm in length with a diameter in the range of about 1.0 to about 1.75 mm. The taper of the post unit is about 0.02 to about 0.06 mm/per mm. Although carrier section 56 is shown as being tapered, it may also be of constant diameter. Post unit 50 may also include a handle 60 which is beneficial when the post unit is used as an obturator. Section 54 of unit 50 within handle 60 may be tapered or straight. Handle 60 may be any filled or unfilled polymeric material, such as those mentioned above and used in the fabrication of the post. The handle may be colored to distinguish between the different sizes.

In yet a further embodiment herein, the post or obturator may comprise a protrusion or a depression on the tip section of the device in order to assist in the attachment of the filler cone to the tip or shaft section. The protrusions and depressions may be in any shape or form including but not limited to spherical, cylindrical, rectangular, oval, and semi-spherical forms. The protrusions and depressions may be comprised of a single protrusion or depression on the tip section or may be comprised of a series of two or more protrusions or depressions disposed uniformly or randomly along the length of the tip section.

Figure 6:
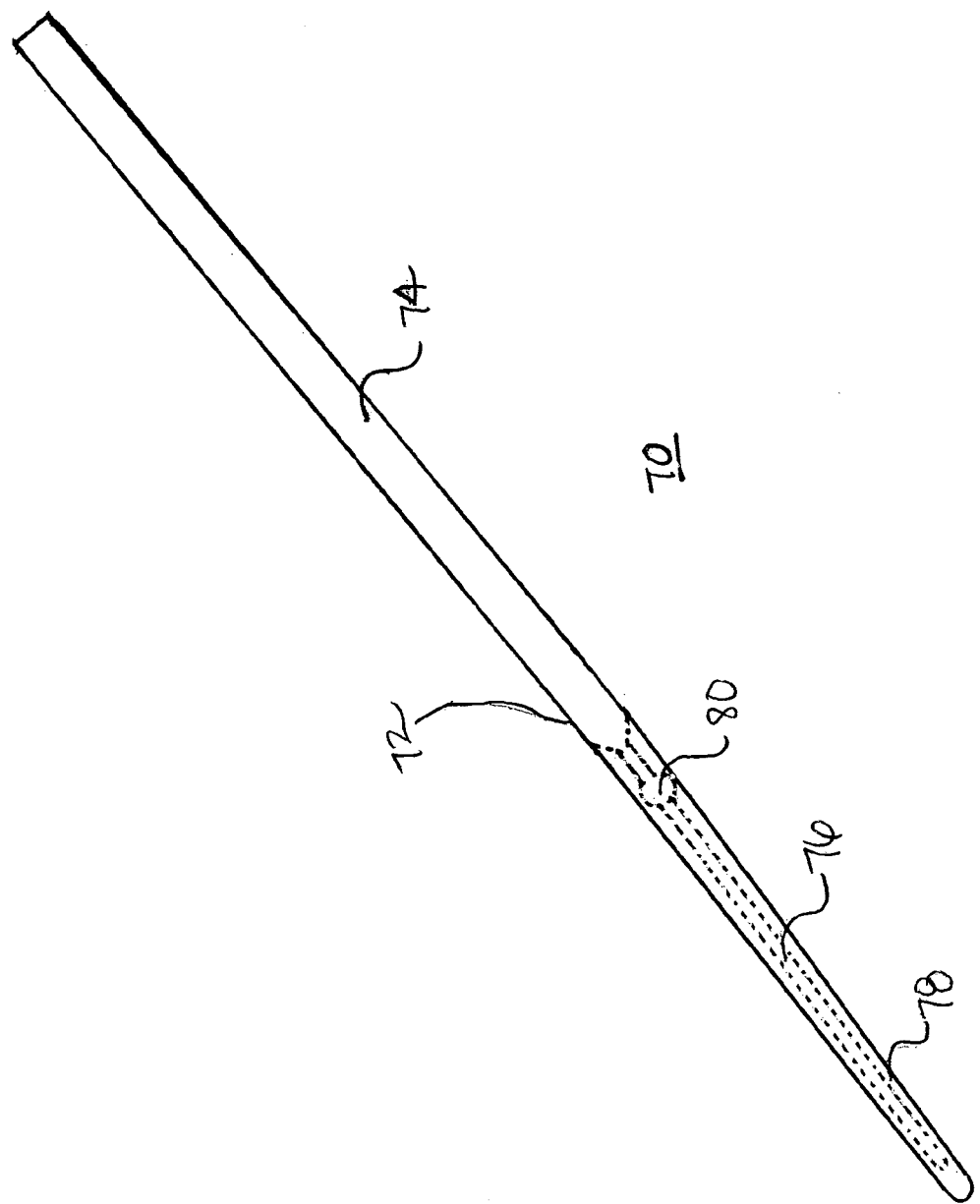
FIG. 6 is an elevational view of an alternate embodiment of a post in accordance with the invention.

Reference is hereby made to FIG. 6, which shows post 70 having a post section 72. As stated above, post section 72 may be fabricated of any known post materials not limited to the aforementioned materials described herein and is preferably fabricated of fiber reinforced composite material. Post section 72 includes main body 74 and carrier 76. Carrier 76 is coated with a filling material such as gutta percha to obtain filler cone section 78 thereon. As shown in the drawing, post section 72 is slightly tapered as is filler cone section 78 to provide ease of placement into the canal. Carrier 76 includes a protrusion in the form of a sphere 80, which protrudes annularly around carrier 76. The cross-section of post 70 may be smaller than the cross-section of a standard post to fit in thinner or smaller auxiliary canals which are normally filled with a thermoplastic material.

Figure 7:
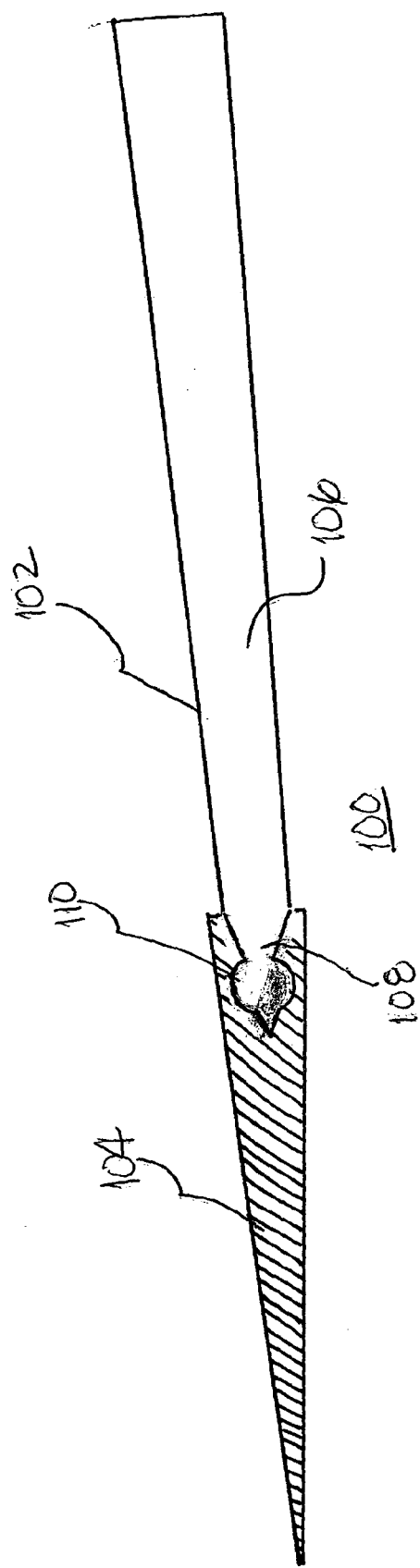
FIG. 7 is an elevational view of an obturator in accordance with the invention.
Figure 8:
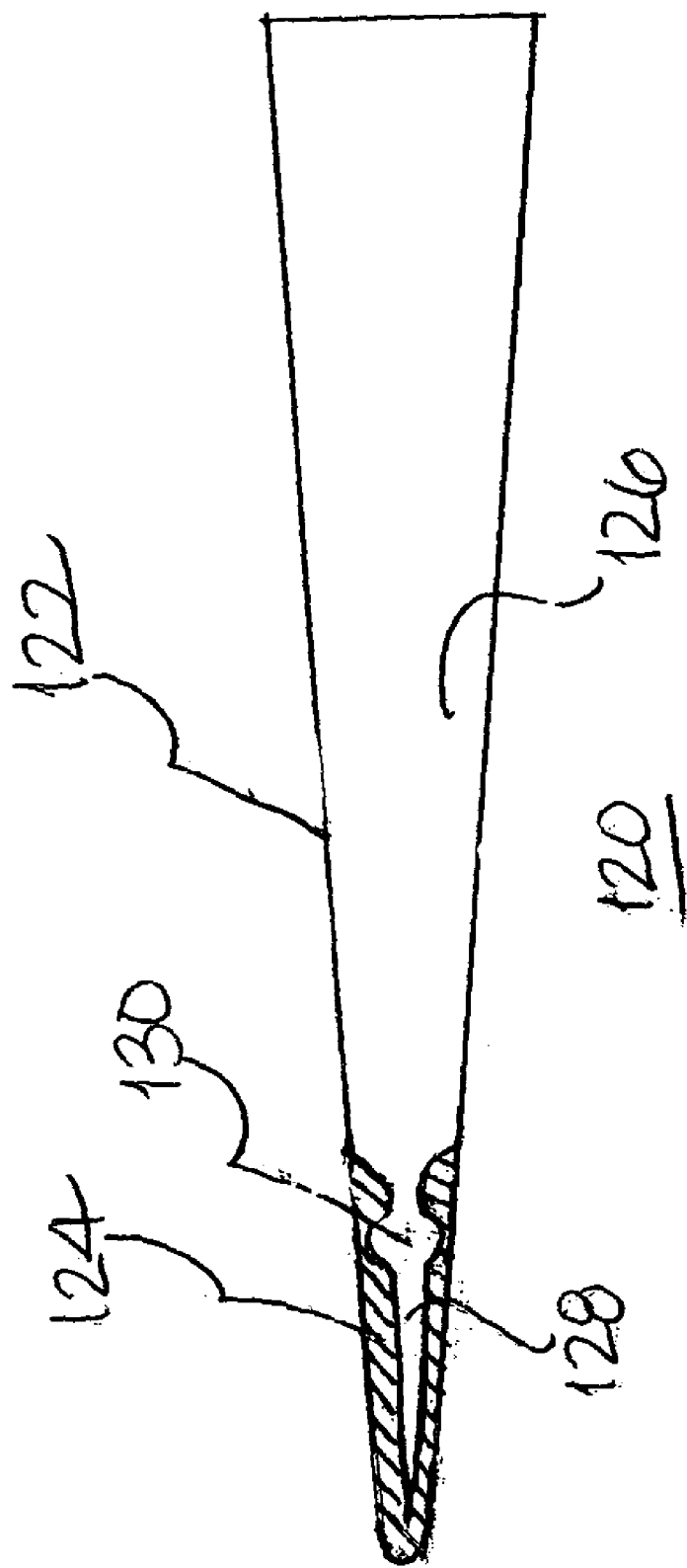
FIG. 8 is an elevational view of an obturator in accordance with the invention.

FIG. 7 is directed to an obturator 100 having a carrier 102 and filling material disposed thereon in the form of a filler cone 104. Carrier 102 includes a handle section 106 and a tip or shaft section 108. A protrusion in the form of a sphere 110 is disposed on shaft section 108 for retaining filler cone 104 thereon. As shown in FIG. 7, shaft section 108 does not extend the length of the filler cone 104. FIG. 8 shows an alternate obturator 120 having a carrier 122 and filling material disposed thereon in the form of a filler cone 124. Carrier 122 includes a handle section 126 and a tip or shaft section 128 for retaining filler cone 124 thereon. A protrusion in the form of a sphere 130 is disposed on shaft section 128 for retaining filler cone 124 thereon. As shown in FIG. 8, shaft section 128 extends the length of filler cone 124. Accordingly, as shown in FIGS. 7 and 8, the shaft section as well as the carrier section may vary in length and width.

Figure 9:
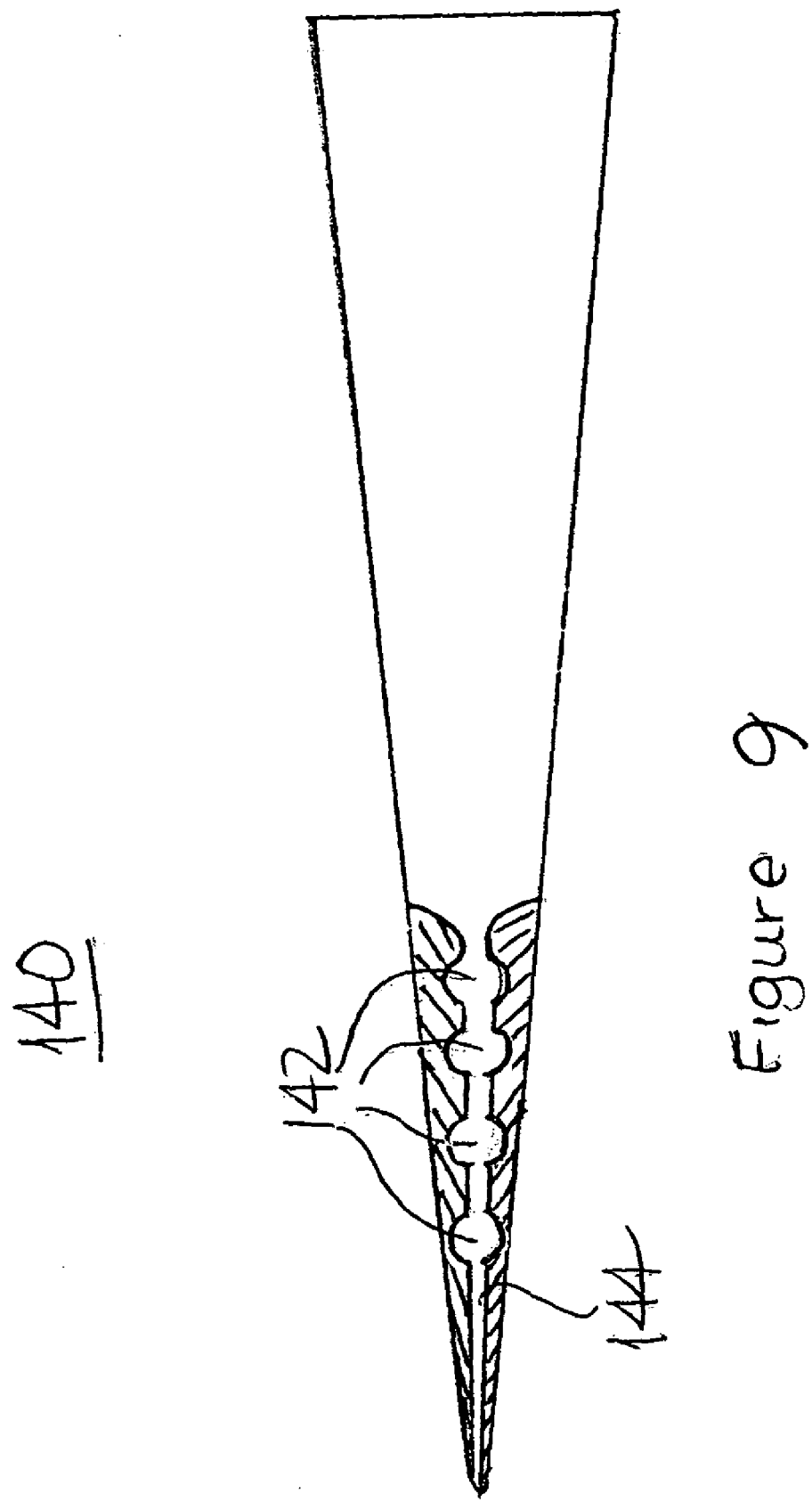
FIG. 9 is an elevational view of an obturator in accordance with the invention.

FIG. 9 shows an alternative embodiment herein. FIG. 9 represents an obuturator 140 having a plurality of protrusions in the shape of spheres 142 extending outwardly on shaft section 144. The carrier of the obturator may be made of any material used in the industry suitable for carriers including the above-mentioned materials used in the fabrication of the posts.

Figure 10:
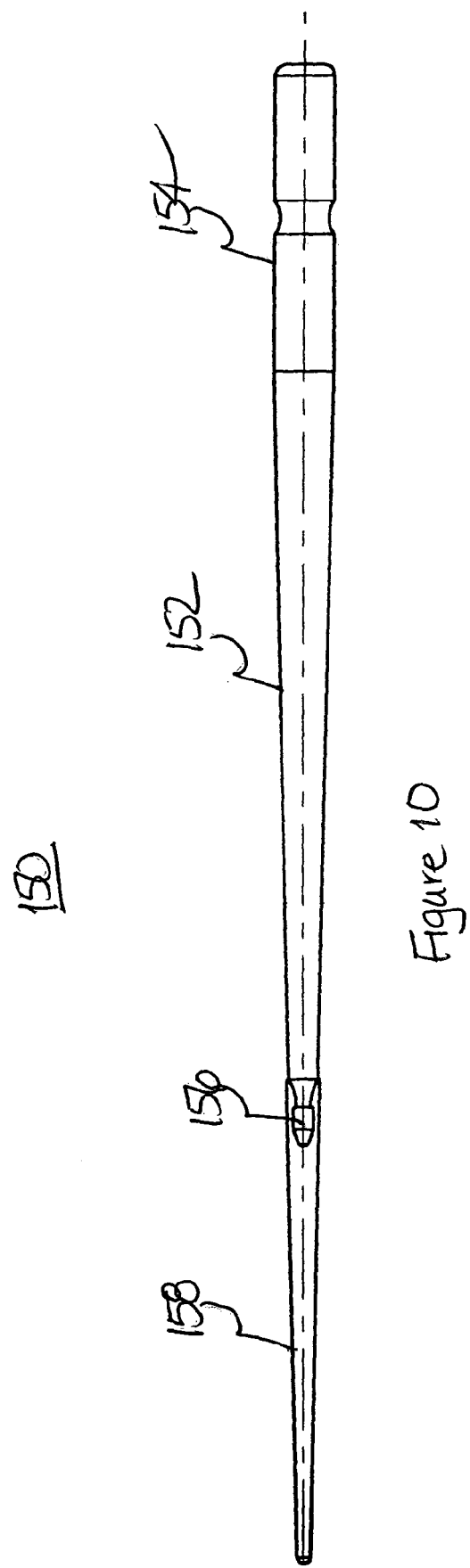
FIG. 10 is an elevational view of an obturator in accordance with the invention.
Figure 11:
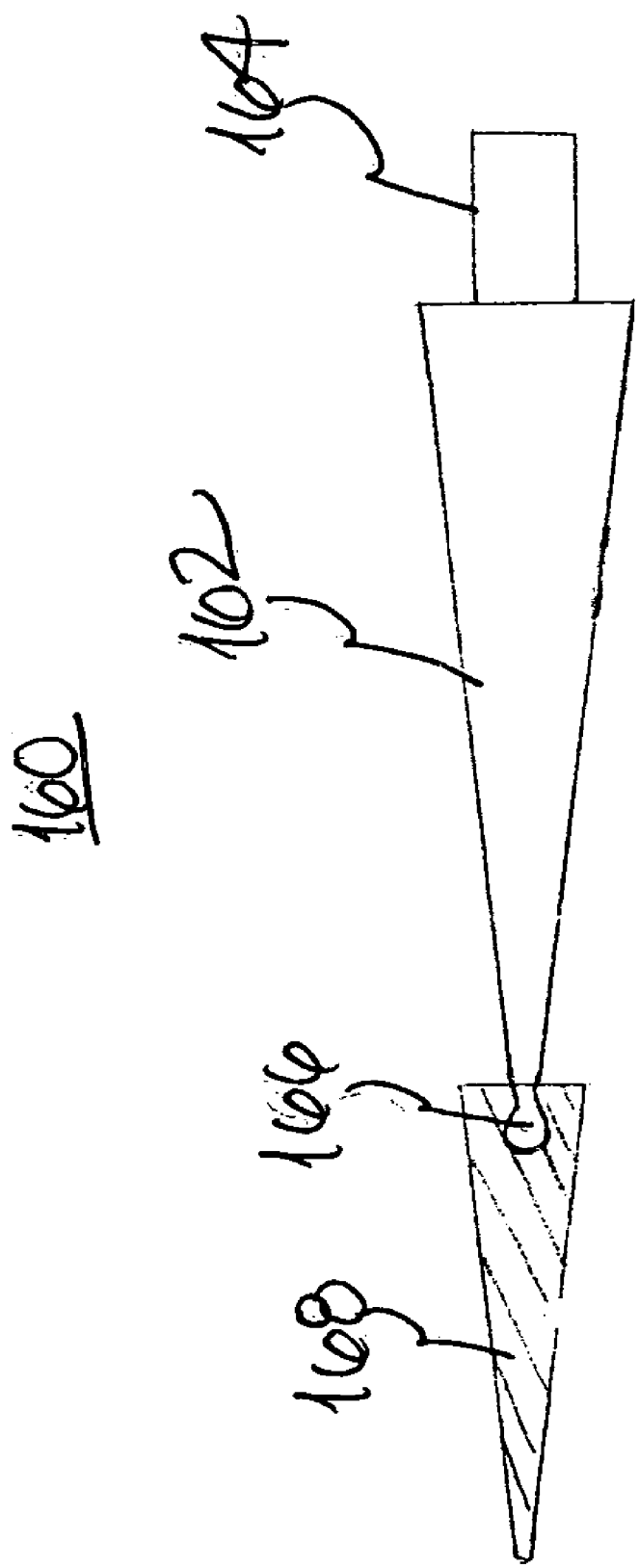
FIG. 11 is an elevational view of an obturator in accordance with the invention.

FIGS. 10 and 11 show more representations of the invention with obturators 150 and 160, respectively, having carriers 152 and 162, respectively, and handles 154 and 164, respectively. Carriers 152 and 162 include protrusions 156 and 166, respectively for retaining filler cones 158 and 168, respectively, thereon.

Figure 12:
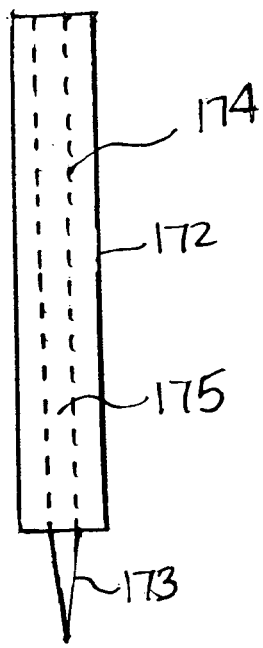
FIG. 12 is an elevational view of a post in accordance with the invention.
Figure 13:
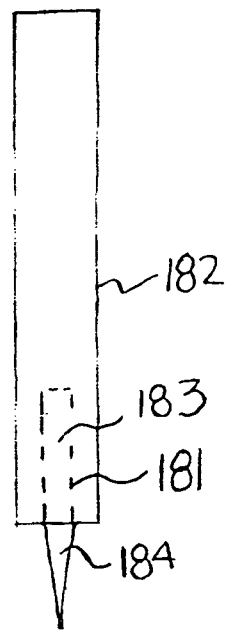
FIG. 13 is an elevational view of a post in accordance with the invention.
Figure 14:
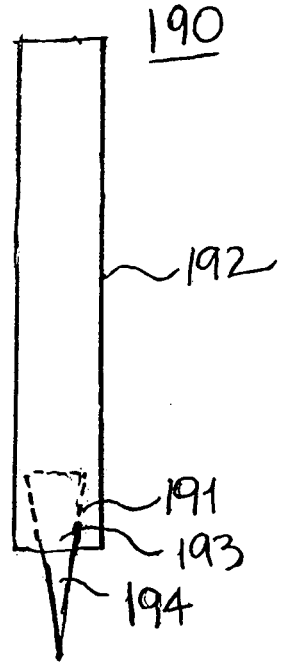
FIG. 14 is an elevational view of a post in accordance with the invention.
Figure 15:
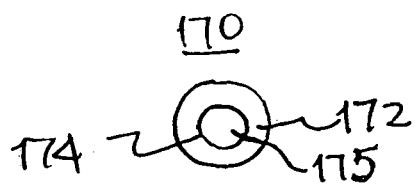
FIG. 15 is a top plan view of FIG. 12.

FIGS. 12 through 15 show alternate embodiments of posts and obturators herein. FIG. 12 shows a post 170 having a rigid endodontic section which is in the form of a shaft 172 and an apical tip section in the form of a filler cone 173. An opening 174 extends through shaft 172. Although opening 174 extends the entire length of shaft 172 in FIG. 12, it is possible that the opening not extend the entire length of shaft 172, but only a portion of shaft 172 as shown as opening 181 in post 180 of FIG. 13 or alternatively as opening 191 in post 190 of FIG. 14. Openings 181 and 191 extend between about one-third to about one-quarter the length of shafts 182 and 192 of posts 180 and 190, respectively, although there is not limitation on how long or short the opening can be. It is preferable that openings 174, 181 and 191 extend centrally through shafts 172, 182 and 192. As seen in FIG. 14, opening 191 is undercut in shaft 192 on an angle which increases in width from the apical point toward the coronal end of the post. This is provided to show that the opening in the shaft is not limited to any size, shape or design, but may be of any form to achieve the design of the post or obturator having an integral filler cone in accordance with the invention herein. Openings 174, 181 and 191 of FIGS. 12 through 14 are filled with a filling material, such as any known material for filling root canals, including but not limited to the materials mentioned herein, to form post interiors or core sections 175, 183 and 193 of the posts in FIGS. 12 through 14, respectively. The filling material extends out of the apical ends of shafts 172, 182 and 192 in FIGS. 12 through 14, respectively, to form filler cones 173, 184 and 194 in FIGS. 12 through 14, respectively. Posts 170, 180 and 190 may be manufactured by first forming a hollow tube or partially hollow/partially solid tube (shafts 182 and 192) fabricated of any known post material, including but not limited to the materials mentioned herein. Alternatively, shafts 172, 182 and 192 may be formed as solid rods which are then machined, drilled, cut or modified by other similar known means to provide openings 174, 181 and 191, respectively. The shaft is then attached to a filler cone mold and a filling material is inserted or injected into the opening and the filler cone mold by any known means, such as, for example, by injection, to form the post core and filler cone. The filling material is cured to form a post having a hardened filler cone integrally attached thereto. The filler cone mold is then removed to provide a post and hardened cone integrally attached thereto. FIG. 15 is a top plan view of FIG. 12 showing the top of post 170 with shaft 172, opening 174 and core section 175.

Figure 16:
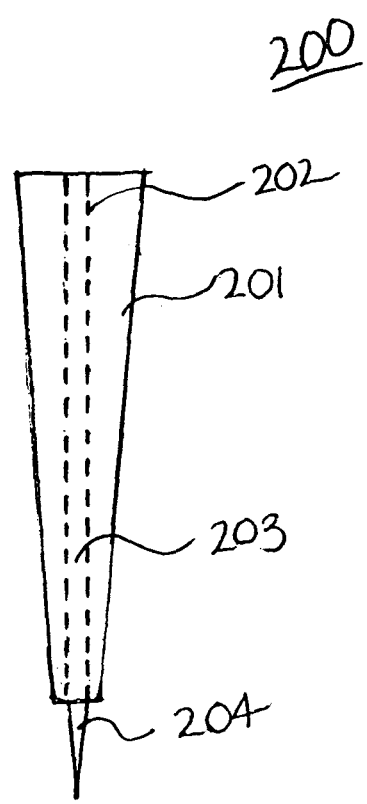
FIG. 16 is an elevational view of an obturator in accordance with the invention.
Figure 17:
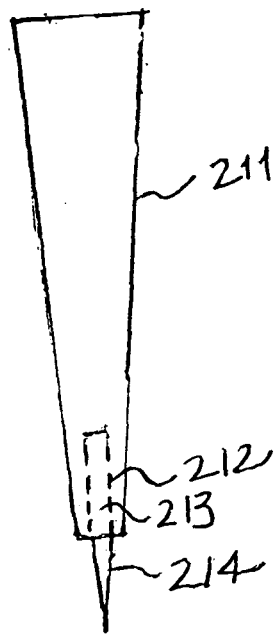
FIG. 17 is an elevational view of an obturator in accordance with the invention.
Figure 18:
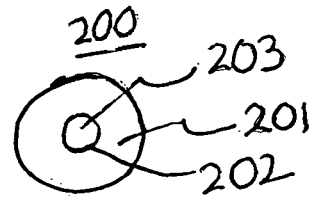
FIG. 18 is a top plan view of FIG. 16.

FIGS. 16 and 17 show alternate embodiments of obturators 200 and 210 having carriers 201 and 211, which may be tapered. The carriers have openings 202 and 212 which extend therethrough. Opening 202 of carrier 201 extends the length of carrier 201 and opening 212 of carrier 211 extends only a portion of the length of carrier 211. Openings 202 and 212 are filled with a filling material, such as any known material for filling root canals, including but not limited to the materials mentioned herein, to form an obturator interior or core section 203 and 213, which filling material extends out of the apical ends of carriers 201 and 211 to form filler cones 204 and 214. Obturators 200 and 210 may be manufactured in the same way as posts 170, 180 and 190 described above, by first forming a tapered shaft or carrier fabricated of any known post material, including but not limited to the materials mentioned herein. The shafts are then attached to a filler cone mold and a filling material is inserted into the tunnel and the filler cone mold to form the obturator core and filler cone. The filling material is cured to form a hardened obturator having a hardened filler cone integrally attached thereto. FIG. 18 is a top plan view of FIG. 16 showing the top of obturator 200 with carrier 201, opening 202 and core section 203.

Figure 19:
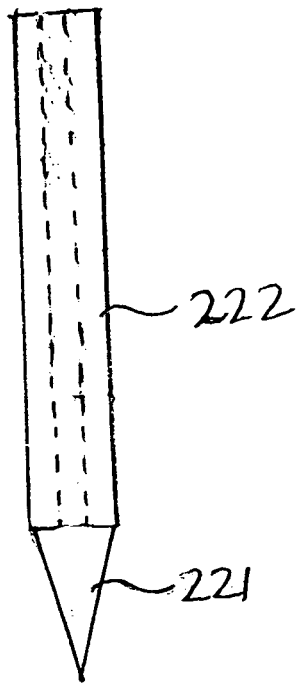
FIG. 19 is an elevational view of a post in accordance with the invention.
Figure 20:
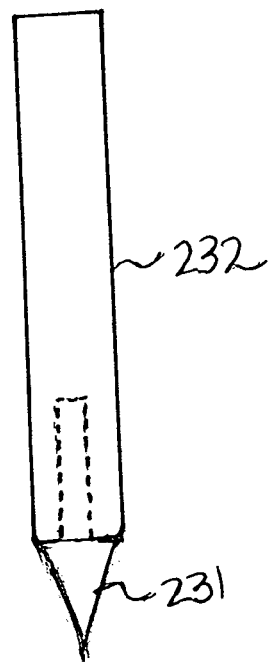
FIG. 20 is an elevational view of a post in accordance with the invention.
Figure 21:
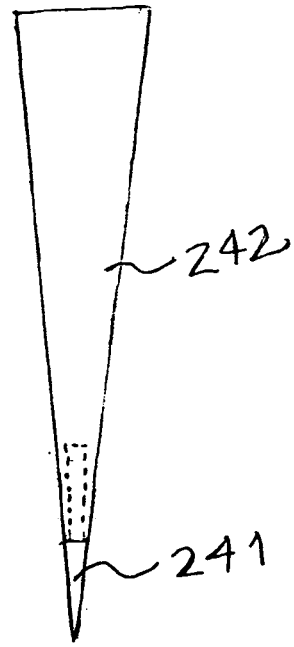
FIG. 21 is an elevational view of an obturator in accordance with the invention.

FIGS. 19 through 21 show yet more alternative embodiments herein. Posts 220 and 230 in FIGS. 19 and 20 show filler cones 221 and 231, respectively, flush with the perimeters of shafts 222 and 232, respectively, at the end of the filler cone that is in contact with the shaft, i.e., the perimeter of the top end of the filler cone is flush with (same as) the perimeter of the bottom end of the shaft. FIG. 21 shows obturator 240 having filler cone 241 flush with the perimeter of carrier 242 at the end of the filler cone that is in contact with the carrier, i.e., the perimeter of the top end of the filler cone is flush with (same as) the perimeter of the bottom end of the carrier. Each of the posts or obturators have an opening in the shaft or carrier for filling material to be injected, which filling material will extend out of the apical end to form the filler cone. The materials and methods of manufacture are the same as mentioned herein for the other embodiments and designs.

In using the posts and obturators described herein, the canal is cleaned and prepared by the dentist. The dentist may or may not soften the filler cone prior to insertion in the canal. The post or obturator is inserted into the canal. Any excess in length of the post or obturator may be trimmed off by the dentist.

While various descriptions of the present invention are described above, it should be understood that the various features can be used singly or in any combination thereof. Therefore, this invention is not to be limited to only the specifically preferred embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An endodontic post comprising:
    a rigid endodontic section and an apical tip section;
    wherein the rigid endodontic section comprises a shaft;
    wherein the shaft comprises an opening extending through the shaft;
    wherein the opening in the shaft comprises filling material therein;
    wherein the filling material extends out of the opening to form the apical tip section.

2. The endodontic post of claim 1 wherein the apical tip section of the post is tapered.

3. The endodontic post of claim 1 wherein the apical tip section of the post is narrower in diameter than the diameter of the endodontic section.

4. The endodontic post of claim 1 wherein the post further comprises a supracoronal portion.

5. The endodontic post of claim 1 wherein the opening extends fully the length of the shaft.

6. The endodontic post of claim 1 wherein the opening extends partially the length of the shaft.

7. The endodontic post of claim 1 wherein the shaft is fabricated of metal, plastic, composite, ceramic, glass or polymeric material.

8. The endodontic post of claim 7 wherein the polymeric material is selected from the group consisting of thermoplastic, thermoset, chemoplastic resins and mixtures thereof.

9. The endodontic post of claim 7 wherein the composite material comprises fiber reinforced composite material.

10. The endodontic post of claim 7 wherein the composite material comprises filler reinforced composite material.

11. The endodontic post of claim 1 wherein the filling material comprises a thermoplastic or chemoplastic material.

12. The endodontic post of claim 1 wherein the filling material comprises a resinous material.

13. The endodontic post of claim 12 wherein the filling material further comprises a plasticizing agent, antibiotic agent, cariostatic agent, antibacterial agent, anti-inflammatory agent, biologically active agent, or therapeutic agent, or mixtures thereof.

14. The endodontic post of claim 1 wherein the filling material comprises gutta percha.

15. The endodontic post of claim 1 wherein the filling material comprises polyacrylate, polyurethane, polypropylene, polyethylene, polyamide, fluoropolymer, polyester, polyphosphazene, polyanhydride, polysulfide, polyether, epoxy, polycarbonate, polystyrene, polybutadiene, polyphenylene oxide, silicone rubber or a mixture thereof.

16. The endodontic post of claim 15 wherein the polyacrylate comprises polymethyl methacrylate, polyhydroxy ethyl methacrylate, or hydroxy ethyl methacrylate (HEMA).

17. The endodontic post of claim 14 wherein the fluoropolymer comprises polytetrafluoroethylene (PTFE) or perfluoroalkoxy (PFA). copolymer resin (PFA).

18. The endodontic post of claim 15 wherein the polyester comprises polylactic acid, glycolide, polycaprolactone or a co-polymer thereof.

19. The endodontic post of claim 15 wherein the wherein the polyester comprises polylactic acid, glycolide, polycaprolactone or a co-polymer thereof.

20. The endodontic post of claim 15 wherein the silicone rubber comprises polysiloxane.

21. The endodontic post of claim 1 wherein the filling material comprises polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyethylene oxides, polyacrylates/methacrylates, polyalkylene succinates, poly(malic acid) polymers, polymaleic anhydrides, poly(methylvinyl) ethers, poly(amino acids), chitin, chitosan, and copolymers, terpolymers, or combinations or mixtures thereof.

22. The endodontic post of claim 1 wherein the perimeter of the filling material is the same as the perimeter of the shaft at the end of the filling material that is in contact with the shaft.

23. A device for filling a root canal comprising:
a carrier; and
a filler cone;
wherein the carrier comprises an opening extending through the carrier;
wherein the opening in the carrier comprises filling material therein; and
wherein the filling material extends out of the opening to form the filler cone.

24. The device of claim 23 wherein the carrier and filler cone are tapered.

25. The device of claim 23 wherein the filler cone is narrower in diameter than the diameter of the carrier.

26. The device of claim 23 wherein the opening extends fully the length of the carrier.

27. The device of claim 23 wherein the opening extends partially the length of the carrier.

28. The device of claim 23 wherein the carrier is fabricated of metal, plastic, composite, ceramic, glass or polymeric material.

29. The device of claim 28 wherein the polymeric material is selected from the group consisting of thermoplastic, thermoset, chemoplastic resins and mixtures thereof.

30. The device of claim 28 wherein the composite material comprises fiber reinforced composite material.

31. The device of claim 28 wherein the composite material comprises filler reinforced composite material.

32. The device of claim 23 wherein the filling material comprises a thermoplastic or chemoplastic material.

33. The device of claim 23 wherein the filling material comprises a resinous material.

34. The device of claim 33 wherein the filling material further comprises a plasticizing agent, antibiotic agent, cariostatic agent, antibacterial agent, anti-inflammatory agent, biologically active agent, or therapeutic agent, or mixtures thereof.

35. The device of claim 23 wherein the filling material comprises gutta percha.

36. The device of claim 23 wherein the filling material comprises polyacrylate, polyurethane, polypropylene, polyethylene, polyamide, fluoropolymer, polyester, polyphosphazene, polyanhydride, polysulfide, polyether, epoxy, polycarbonate, polystyrene, polybutadiene, polyphenylene oxide, silicone rubber or a mixture thereof.

37. The device of claim 36 wherein the polyacrylate comprises polymethyl methacrylate, polyhydroxy ethyl methacrylate, or hydroxy ethyl methacrylate (HEMA).

38. The device of claim 36 wherein the fluoropolymer comprises polytetrafluoroethylene (PTFE) or perfluoroalkoxy copolymer resin PFA.

39. The device of claim 36 wherein the polyester comprises polylactic acid, glycolide, polycaprolactone or a co-polymer thereof.

40. The device of claim 36 wherein the wherein the polyester comprises polylactic acid, glycolide, polycaprolactone or a co-polymer thereof.

41. The device of claim 36 wherein the wherein the silicone rubber comprises polysiloxane.

42. The device of claim 23 wherein the filling material comprises polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyethylene oxides, polyacrylates methacrylates, polyalkylene succinates, poly(malic acid) polymers, polymaleic anhydrides, poly(methylvinyl) ethers, poly(amino acids), chitin, chitosan, and copolymers, terpolymers, or combinations or mixtures thereof.

43. The device of claim 23 wherein the perimeter of the filler cone is the same as the perimeter of the carrier at the end of the filler cone that is in contact with the carrier.

44. A method for restoring the root canal of a tooth comprising:
preparing the root canal;
providing a post for insertion into the canal, whereby the post comprises a post section, the post section comprising a rigid endodontic section and an apical tip section, wherein the rigid endodontic section comprises a shaft, wherein the shaft comprises an opening extending through the shaft, wherein the opening in the shaft comprises filling material therein, and wherein the filling material extends out of the opening to form the apical tip section; and
inserting the post into the canal, whereby the apical end of the root canal is filled by the apical tip section.

45. The method of claim 44 wherein the apical tip section is softened prior to insertion of the post into the canal.

46. The method of claim 44 further comprising inserting a sealing material into the canal to bond the post to the canal prior to insertion of the post into the canal.

47. The method of claim 44 further comprising building a core on an end of the post that extends from the canal.

48. The method of claim 47 further comprising placing a crown on the core.

49. The method of claim 47 further comprising filling the tooth with composite material to complete the process.

50. A method for restoring the root canal of a tooth comprising:
preparing the root canal;
providing a device for filling a root canal whereby the device comprises a carrier and a filler cone, wherein the carrier comprises an opening extending through the carrier, wherein the opening in the carrier comprises filling material therein, and wherein the filling material extends out of the opening to form the filler cone;

inserting the carrier into the canal, whereby the apical end of the root canal is filled by the filler cone; and removing the carrier from the filler cone.

51. The method of claim 50 wherein the entire carrier is removed from the filler cone.

52. The method of claim 50 wherein a portion of the carrier is removed from the filler cone.

53. The method of claim 50 wherein the filler cone is softened prior to insertion of the carrier into the canal.

54. The method of claim 50 further comprising injecting a sealing material into the canal to bond the filler cone to the canal prior to insertion of the carrier into the canal.

* * * * *